United States Patent [19]

Sustmann

[11] Patent Number: 4,642,108
[45] Date of Patent: Feb. 10, 1987

[54] TAMPON FOR FEMININE HYGIENE AND A PROCESS FOR ITS PRODUCTION

[75] Inventor: Scarlet Sustmann, Viersen, Fed. Rep. of Germany

[73] Assignee: Vereinigte Papierwerke, Schickedanz & Co., Nuremberg, Fed. Rep. of Germany

[21] Appl. No.: 799,279

[22] Filed: Nov. 19, 1985

Related U.S. Application Data

[63] Continuation of Ser. No. 536,175, Sep. 27, 1983, abandoned.

[30] Foreign Application Priority Data

Oct. 2, 1982 [DE] Fed. Rep. of Germany ....... 3236540

[51] Int. Cl.$^4$ ............................................. A61F 13/16
[52] U.S. Cl. .................... 604/379; 604/358; 604/904
[58] Field of Search ............... 604/377, 379, 378, 385, 604/904

[56] References Cited

U.S. PATENT DOCUMENTS

| | | | |
|---|---|---|---|
| 3,051,177 | 8/1962 | Wilson et al. | 128/285 |
| 4,095,542 | 6/1978 | Hirschman | 604/377 |
| 4,294,253 | 10/1981 | Friese | 604/904 |

FOREIGN PATENT DOCUMENTS

| | | |
|---|---|---|
| 1491235 | 6/1969 | Fed. Rep. of Germany . |
| 2855179 | 6/1980 | Fed. Rep. of Germany . |
| 594061 | 6/1945 | United Kingdom . |
| 844676 | 2/1959 | United Kingdom . |
| 855119 | 11/1960 | United Kingdom . |

*Primary Examiner*—C. Fred Rosenbaum
*Assistant Examiner*—Sherri E. Vinyard
*Attorney, Agent, or Firm*—Ernest G. Szoke; Henry E. Millson, Jr.; Mark A. Greenfield

[57] ABSTRACT

A tampon for feminine hygiene consists of a cylindrically-compressed length of a strip of cottonwool or rayon staple or a combination thereof which is wrapped with an overlap in a fluff-free or fuzz free covering material, said strip being cut into the required lengths together with the covering material perpendicularly to the overlap line, and a recovery thread attached to the length of a strip of cottonwool or rayon staple or a combination thereof. The problem which the invention solves is to prevent fibers from breaking loose from the exposed cut edges. According to the invention, the exposed cut edges are folded onto the surface of the length of a strip of cottonwool or rayon staple or a combination thereof after it has been separated and compression is carried out in such a way that the exposed cut edges are situated inside the tampon.

12 Claims, 19 Drawing Figures

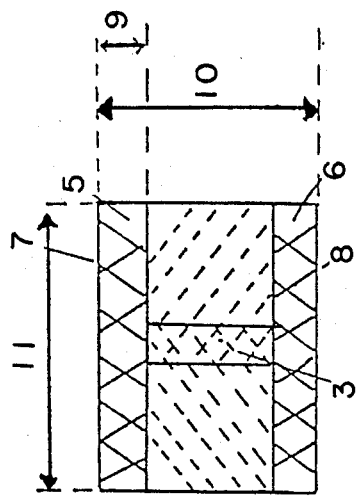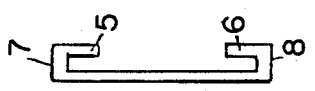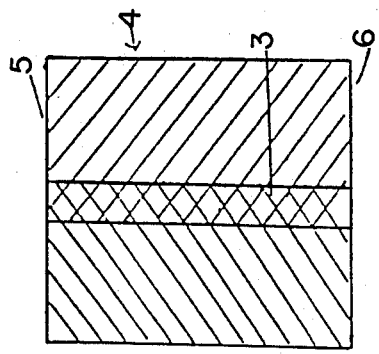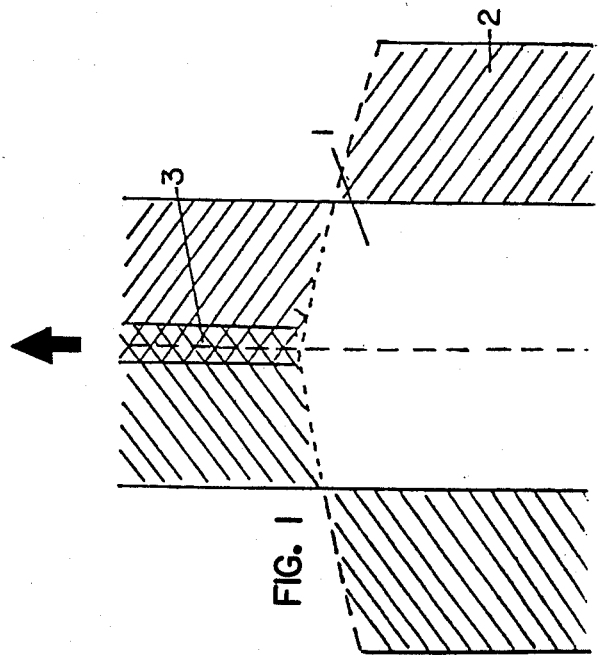

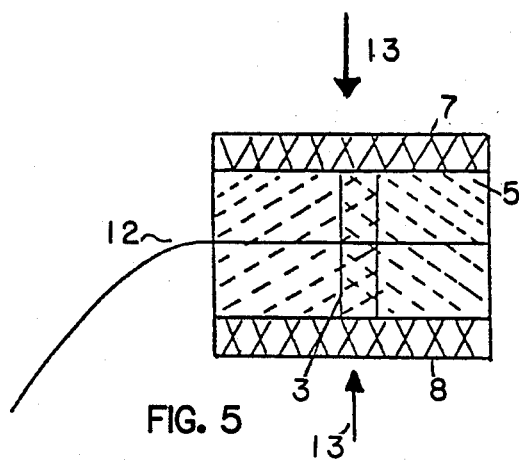
FIG. 5
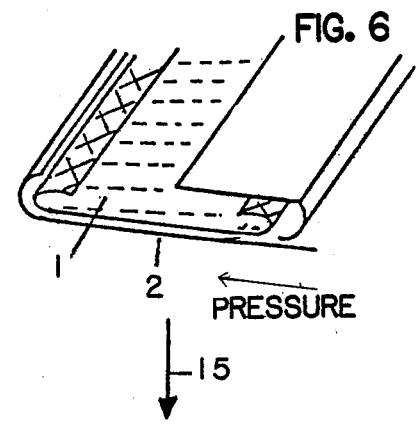
FIG. 6
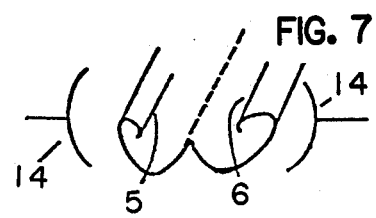
FIG. 7
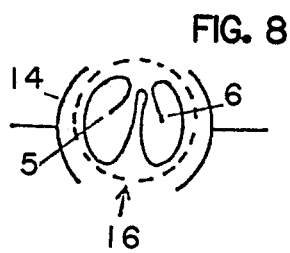
FIG. 8
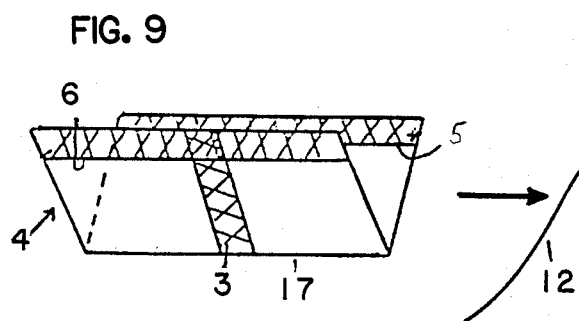
FIG. 9
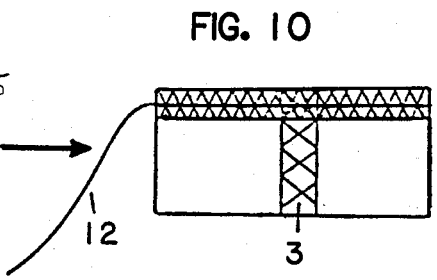
FIG. 10

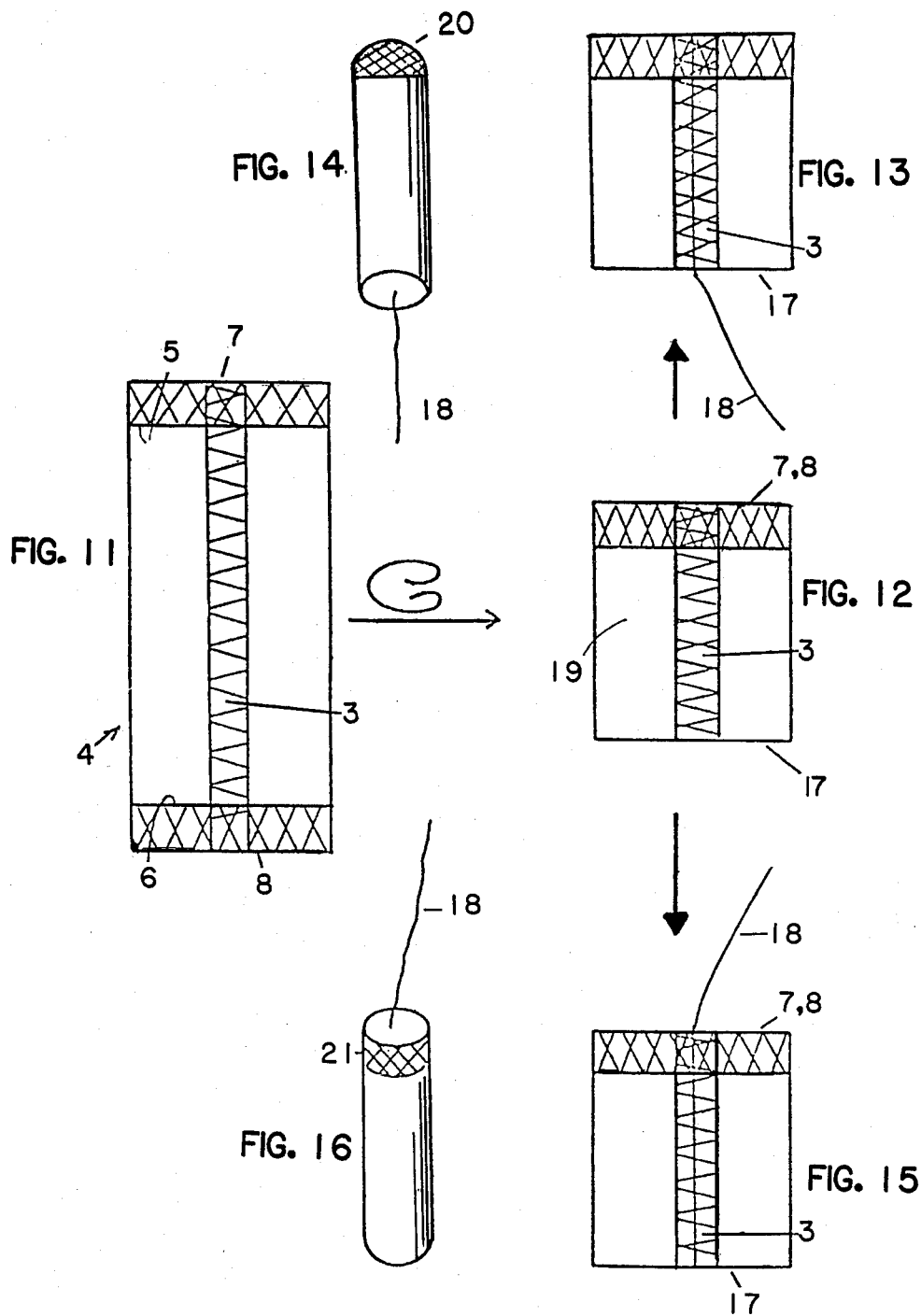

TAMPON FOR FEMININE HYGIENE AND A PROCESS FOR ITS PRODUCTION

This application is a continuation of application Ser. No. 536,175, filed Sept. 27, 1983 now abandoned.

BACKGROUND OF THE INVENTION

This invention relates to a tampon for feminine hygiene consisting of a length of a strip of cottonwool or rayon staple or combination thereof which is wrapped with overlap in a fluff-free or fuzz-free covering material and then cut into the desired lengths together with the covering material substantially perpendicularly of the overlap line and which is provided with a recovery thread applied parallel to or perpendicularly of the overlap line. After folding the cut edges, the tampon is compressed radially and/or axially relative to the overlap line. The invention also relates to a process for producing the tampon.

With conventional tampons, fibers or pieces of cottonwool can remain behind in the vagina. Accordingly, attempts have been made to cover the length of a fibrous strip of cottonwool or rayon staple or a combination thereof with moisture-pervious fluff-free or fuzz-free material during the manufacture of tampons. The covering in question may consist, for example, of rayon, synthetic fibers or of a mixture of these materials, preferably in a nonwoven form. For example, tampons are produced by a process in which the rectangular length of a strip of cottonwool or rayon staple or combination thereof is wrapped in a nonwoven and the associated recovery thread or recovery string is sewn on longitudinally of the strip. In that case, compression may be carried out radially and/or axially in relation to the longitudinal axis of the strip. Where compression is carried out radially, W-shaped folding, i.e. four-layer, folding is preferred. However, this process does not enable the tampon to be covered at its cut edges, i.e. at the head of the tampon and at its end, so that fibers are able to break loose there, that is, to break out from the cottonwool strip strip of cottonwool or rayon staple or combination thereof.

In another process used for producing tampons, the strip of cottonwool strip of cottonwool or rayon staple or combination thereof is wrapped in a nonwoven and then cut into rectangular sections. The length of the section to be compressed is determined by the width of the cottonwool strip strip of cottonwool or rayon staple or combination thereof. Accordingly, the recovery thread is fastened perpendicularly of, rather than parallel to, the overlap line of the covering material. In this process, too, W-shaped folding of the covered section of cottonwool strip strip of cottonwool or rayon staple or combination thereof is preferred, although the fold lines run parallel to the exposed cut edges. In this way, the exposed cut edges are displaced from the head and the end of the tampon onto its substantially cylindrical peripheral surface, although they are still exposed. Accordingly, fibers can become detached from the cut edges on removal of the tampon, particularly after it has expanded on taking up fluid.

OBJECTS OF THE INVENTION

An object of the present invention is to provide a tampon which is completely covered by a fluff-free or fuzz-free material in such a way that no fibers are able to break loose when the tampon is in use.

Another object of the present invention is the development of a tampon for female hygiene consisting essentially of a length of a strip of cottonwool or rayon staple or combination thereof which is wrapped with an overlap in a moisture-pervious fluff-free or fuzz-free covering material, said strip being cut into the required lengths, together with the covering material, perpendicularly to the overlap line, and a recovery thread attached to the strip of cottonwool or rayon staple or a combination thereof, which length is then compressed cylindrically characterized in that, before said compression, the exposed cut edges running perpendicularly to the overlap line are folded onto the surface of the covered length of cottonwool or rayon staple or a combination thereof and said covered length of cottonwool or rayon staple or a combination thereof is folded, whereby, after compression, the inwardly folded cut edges are inside the tampon.

A yet further object of the present invention is the development of the improvement in a process for the production of a tampon for female hygiene comprising the steps of:

(1) wrapping a strip of cottonwool or rayon staple or a combination thereof with an overlap in a moisture-pervious, fluff-free or fuzz-free covering material, (2) cutting said covered strip into the desired length, perpendicularly to the overlap line, (3) attaching a recovery thread to said length of covered strip, and (4) compressing said length of covered strip cylindrically, the improvement consisting essentially of, before compressing, folding the exposed cut edges running perpendicularly to the overlap line onto the surface of the length of covered strip, and folding said covered length of cottonwool, whereby, after said compressing cylindrically, the inwardly folded cut edges are inside the tampon.

These and other objects of the invention will become more apparent as the description proceeds.

THE DRAWINGS

FIGS. 1 to 4 illustrate the sequential steps in the production of the tampon of the invention through the step where the exposed cut edges are folded over.

FIGS. 5 to 8 illustrate the further sequential steps through W-folding and compression in the production of the tampon with the recovery thread running parallel to the exposed cut edges.

FIGS. 9 and 10 illustrate another folding of the length of covered strip before compression.

FIGS. 11 to 16 illustrate folding and compression in the production of the tampon where the cottonwool is more dense at the head or end of the tampon.

DESCRIPTION OF THE INVENTION

Figure 17:
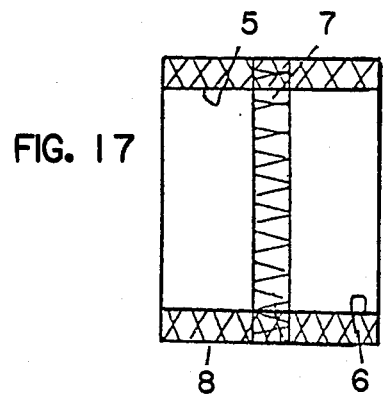
FIGS. 17 to 19 illustrate folding and compression in the production of the tampon where the cottonwool is more dense at both the head and end of the tampon.

More particularly, the problem which the invention seeks to solve is to guarantee all-round moisture-pervious, fluffproof covering of the tampon by special folding of a length of a covered strip of cottonwool or rayon staple or a combination thereof.

For the tampon of a length of a strip of cottonwool or rayon staple or a combination thereof wrapped with overlap in a moisture-pervious, fluffproof or covering material, the solution provided by the invention is characterized in that, before compression, the exposed cut edges running perpendicularly of the overlap line are folded onto the surface of the length of said covered strip and in that the inwardly folded cut edges are situated inside the compressed tampon.

The invention, therefore, relates to a tampon for female hygiene consisting essentially of a cylindrically-compressed length of a strip of cottonwool or rayon staple or a combination thereof which is wrapped with an overlap in a moisture-pervious fluff-free covering material, said strip being cut into the required lengths, together with the covering material, perpendicularly to the overlap line, and a recovery thread attached to the strip of cottonwool or rayon staple or a combination thereof characterized in that, before said compression, the exposed cut edges running perpendicularly to the overlap line are folded onto the surface of the covered length of cottonwool and said covered length of cottonwool is folded, whereby, after compression, the inwardly folded cut edges are inside the tampon.

The invention also relates to a process for the production of a tampon for female hygiene comprising the steps of:

(1) wrapping a strip of cottonwool or rayon staple or a combination thereof with an overlap in a moisture-pervious, fluff-free covering material, (2) cutting said covered strip into the desired length, perpendicularly to the overlap line, (3) attaching a recovery thread to said length of covered strip, and (4) compressing said length of covered strip cylindrically, the improvement consistent essentially of, before compressing, folding the exposed cut edges running perpendicularly to the overlap line onto the surface of the covered length of cottonwool, and folding said covered length of cottonwool, whereby, after cylindrically-compressing, the inwardly folded cut edges are inside the tampon.

The process according to the invention for producing a tampon such as described above is characterized in that the cut edges which remain exposed after separation of the length of a strip of cottonwool or rayon staple or a combination thereof covered with overlap are folded inwards by means of folding plates and pressed down by calender rollers and in that the length of a strip of cottonwool or rayon staple or a combination thereof is then folded and compressed in such a way that the cut edges are situated inside the compressed tampon. In a preferred embodiment, after cutting the covered strip into the desired length, the covered length of cottonwool is transported perpendicularly of the longitudinal axis of the cottonwool strip to the folding station supplied with the folding plates.

According to the invention, all-round covering of the tampon is obtained by virtue of the fact that the cut edges which remain exposed after covering of the strip of cottonwool or rayon staple or a combination thereof with a moisture-pervious, fluff-free or fuzz-free material (i.e. a material which is also fluffproof with respect to the constituent material of the cottonwool strip) are also folded and pressed onto the surface of the covered cottonwool strip. So far as the production process is concerned, this necessitates the inclusion of a corresponding process step in which the separated and covered strip continues its travel, preferably in a direction perpendicular to the longitudinal axis of the strip, on a guide belt where it is folded over and pressed down at the exposed edges by means of baffle plates. All the other operations involved in the production of the tampon may then be carried out in the usual way with hardly any changes.

Embodiments of the invention are described by way of example in the following with reference to the accompanying drawings, wherein:

FIGS. 1 to 4 illustrate the production of a tampon up to the step where the exposed cut edges are folded over.

FIGS. 5 to 8 illustrate the compression of the tampon with the recovery thread running parallel to the exposed cut edges.

FIGS. 9 to 10 illustrate an additional folding of the length of the covered strip of cottonwool or rayon staple or a combination thereof before compression.

FIGS. 11 to 16 show the folding and compression of the tampon where the cottonwool is more dense at the head or end of the tampon.

Figure 18:
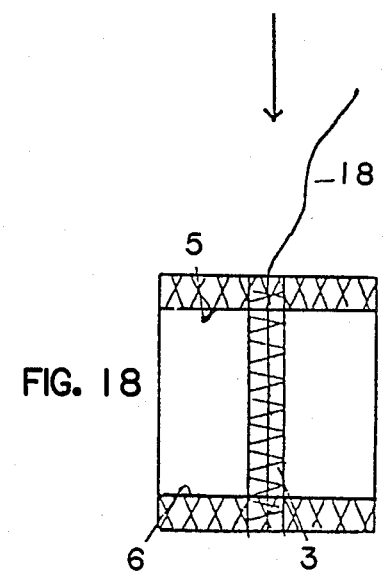
Figure 19:
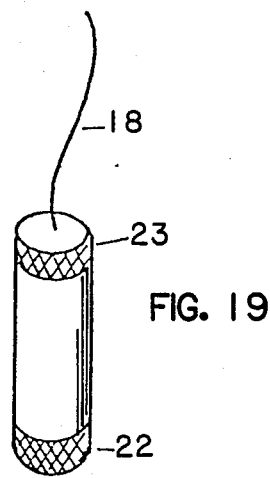

FIGS. 17 to 19 illustrate the production of a tampon in which the cottonwool is more dense at the head and the end of the tampon.

In the production steps taking place one after the other in the arrowed direction in FIGS. 1 to 4, a strip of cottonwood or rayon staple or a combination thereof is delivered on a strip 2 consisting of a moisture-pervious, fluff-free or fuzz-free and also fluffproof or fuzz proof (i.e. with respect to the strip of cottonwood or rayon staple or a combination thereof material to a folding station in which the strip of covering material 2 is wrapped around the strip 1 in such a way that the strip 1 is covered with an overlap 3 at the longitudinal edges. The fluff-free or fuzz-free covering material 2 should have a relatively low weight per unit area of preferably less than 15 g/m$^3$. The cottonwool strip strip of cottonwood or rayon staple or a conbination thereof 1 thus covered then passes to a cutting station where covered lengths 4 of cottonwool strip strip of cottonwood or rayon staple or a combination thereof are formed with exposed cut edges 5 and 6, as shown in FIG. 2.

The lengths 4 of cottonwool strip strip of cottonwood or rayon staple or a combination thereof covered in fluff-free or fuzz-free form up to the exposed cut edges 5 and 6 then pass perpendicularly to their previous direction of travel into an arrangement comprising folding plates (not shown) in which the exposed cut edges 5 and 6 are folded inwards in the manner diagrammatically illustrated in cross-section and in plan view in FIGS. 3 and 4. The overlap line 3 formed in the production phase illustrated in FIG. 1 is then substantially perpendicular to the fold lines 7 and 8 formed by the folding-over of the exposed cut edges 5 and 6. The fold lines 7 and 8 are best pressed in by means of a calender roll. The width of the fold 9 may be selected as required and may amount for example to as much as one sixth of the distance 10 between the fold lines 7 and 8. However, it is also possible inter alia for the fold to overlap. The other parameters namely the distance 10 between the fold lines 7 and 8 and the length 11 in FIG. 4 and also the weight per unit area of the cottonwool strip strip of cottonwood or rayon staple or a combination thereof used, have to be determined according to the width of the fold 9 and the further processing envisaged.

Further processing may be carried out in various ways. As shown in FIGS. 5 to 8 and 9 and 10, the recovery thread is applied, preferably by sewing, to the covered length 4 of cottonwool strip strip of cottonwood or rayon staple or a combination thereof parallel to the fold lines 7 and 8. According to FIGS. 11 to 19, the recovery thread is applied to the covered length 4 of cottonwool strip strip of cottonwood or rayon staple or a combination thereof perpendicularly of the fold lines 7 and 8, i.e. parallel to the overlap line 3.

In the production process illustrated in FIGS. 5 to 8, the covered length 4 of cottonwool strip strip of cottonwood or rayon staple or a combination thereof folded over at the exposed cut edges 5 and 6 and provided with a recovery thread is compressed in the direction of the arrow 13 in the manner illustrated in FIGS. 5 to 8, for example in a chamber by means of two curved jaws 14. This results in a W-shaped fold 15 inside which the exposed cut edges 5 and 6 are situated. The circularly compressed tampon 16 is shown in cross-section in FIG. 8. Thereafter, the tampon 16 may also be axially compressed (perpendicularly of the plane of the drawing) in the usual way. It is completely covered by fluff-free or fuzz-free and fluffproof or fuzz-proof material over its surfaces which come into contact with the walls of the vagina.

Another possible method of folding the tampon is shown in FIGS. 9 and 10. In this case, the covered length 4 of cottonwool strip strip of cottonwood or rayon staple or a combination thereof folded over at the exposed cut edges 5 and 6 is folded once more—before compression—in the longitudinal direction about a fold line 17 extending parallel to the cut edges 5 and 6 so that the cut edges 5 and 6 are situated on the inside. To fix the surfaces which then lie one on top of the other, the recovery thread 12 is preferably sewn on asymmetrically, as shown in FIG. 10. In this way, the sides are held together. At the same time, this ensures that, with a partial fold of length 9, a minimum of covering material 2 is situated inside the tampon. The tampon is then axially compressed in the usual way, so that once again all-round covering of the tampon is guaranteed.

Whereas the process steps described in the foregoing ultimately produce tampons characterized by substantially uniform distribution of the absorbent material, a tampon containing more cotton wool at its head and/or at its end than elsewhere can be produced by modifying the covered length 4 of cottonwool strip, strip of cottonwood or rayon staple or a combination thereof for example by turning it through 90°, naturally without affecting the all-round covering. In that case, the dimensions of the length 4 of cottonwool strip used must of course be adapted to requirements. Corresponding process steps are diagrammatically illustrated in FIGS. 11 to 19. Essentially, the object is to apply the recovery thread 18 to the covered length 4 of cottonwool strip strip of cottonwood or rayon staple or a combination thereof substantially perpendicularly of, rather than parallel to, the inwardly folded, exposed cut edges 5 and 6. To that end, the length 4 of cottonwool strip has to be deflected once again before the recovery thread 18 is applied, i.e. before entry into the machine used for applying the recovery thread, more particularly a sewing machine.

Where a covered length 4 of cottonwool strip strip of cottonwood or rayon staple or a combination thereof turned in at the exposed cut edges 5 and 6 is used to begin with with, as shown in FIG. 11, it may first be folded together on fold line 17 (as in FIG. 9), so that the intermediate product 19 shown in FIG. 12 is formed. The recovery thread 18 is then sewn onto the intermediate product 19 either in such a way that it projects beyond the fold line 17, as shown in FIG. 13, or beyond the fold line 7,8, as shown in FIG. 15. In this way, the tampon obtained either has a safety zone 20 at its upper end, or head, as shown in FIG. 14, or a safety zone 21 at its lower end, as shown in FIG. 16.

If, by contrast, the length 4 of cottonwool strip strip of cottonwood or rayon staple or a combination thereof is not folded at the transition between FIGS. 11 and 12 and if, as shown in FIG. 17, the recovery thread 18 is applied to the unfolded, covered length 4 of cottonwool strip strip of cottonwood or rayon staple or a combination thereof turned inwards at the exposed cut edges 5 and 6—substantially parallel to the overlap line 3 in FIG. 18, the tampon obtained has denser zones both at its head 22 and at its end 23, as shown in FIG. 19.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. In a process for the production of a tampon for female hygiene comprising the steps of
   (1) wrapping a continuous strip of cottonwool or rayon staple or a combination thereof in a moisture-pervious, fluff-free or fuzz-free covering material, said covering material having overlapping edge portions forming an overlap line,
   (2) cutting said continuous length of wrapped strip into the desired individual length, perpendicularly to the overlap line,
   (3) attaching a recovery thread to said individual length of wrapped strip, and
   (4) compressing said individual length of said wrapped strip cylindrically,
   the improvement consisting essentially of, before compressing, the exposed cut edges running perpendicularly to said overlap line are folded onto the surface of said individual length of said wrapped strip of cottonwool or rayon staple or a combination thereof to cover up to about one sixth of the length of said individual length of said wrapped strip after folding, and folding said individual length of said wrapped strip of cottonwool or rayon staple or a combination thereof, whereby, after said compressing cylindrically, the inwardly folded cut edges are inside the tampon.

2. The process for the production of a tampon of claim 1 wherein, after cutting said continuous length of wrapped strip into the desired individual length, the individual length of said wrapped strip of cottonwool or rayon staple or a combination thereof is transported perpendicularly of the longitudinal axis of the individual length of said wrapped strip of cottonwool or rayon staple or a combination thereof to said folding of the exposed cut edges step.

3. The process of claim 1 wherein the wrapped and folded strip of step (1) is compressed to a uniform thickness prior to step (4).

4. The process of claim 2 wherein the wrapped and folded strip of step (1) is compressed to a uniform thickness prior to step (4).

5. The process of claim 1 wherein the wrapped and folded strip of step (1) is folded in a W-fold prior to step (4).

6. The process of claim 2 wherein the wrapped and folded strip of step (1) is folded in a W-fold prior to step (4).

7. The process of claim 3 wherein the wrapped and folded strip of step (1) is folded in a W-fold prior to step (4).

8. The process of claim 4 wherein the wrapped and folded strip of step (1) is folded in a W-fold prior to step (4).

9. The process of claim 1 wherein the wrapped and folded strip of step (1) is folded in a single fold parallel to the exposed cut edges and said recovery thread is applied asymmetrically, but parallel to and coinciding with, said folded cut edges, prior to step (4).

10. The process of claim 2 wherein the wrapped and folded strip of step (1) is folded in a single fold parallel to the exposed cut edges and said recovery thread is applied asymmetrically, but parallel to and coinciding with, said folded cut edges, prior to step (4).

11. The process of claim 3 wherein the wrapped and folded strip of step (1) is folded in a single fold parallel to the exposed cut edges and said recovery thread is applied asymmetrically, but parallel to and coinciding with, said folded cut edges, prior to step (4).

12. The process of claim 4 wherein the wrapped and folded strip of step (1) is folded in a single fold parallel to the exposed cut edges and said recovery thread is applied asymmetrically, but parallel to and coinciding with, said folded cut edges, prior to step (4).

* * * * *